(12) United States Patent
Schneider et al.

(10) Patent No.: US 7,672,462 B2
(45) Date of Patent: Mar. 2, 2010

(54) METHOD AND SYSTEM FOR ACOUSTIC SHOCK PROTECTION

(75) Inventors: Todd Schneider, Ontario (CA); Robert L. Brennan, Ontario (CA); David Hermann, Ontario (CA); Tina Soltani, Ontario (CA)

(73) Assignee: AMI Semiconductor, Inc., Pocatello, ID (US)

( * ) Notice: Subject to any disclaimer, the term of this patent is extended or adjusted under 35 U.S.C. 154(b) by 1614 days.

(21) Appl. No.: 10/815,891

(22) Filed: Mar. 31, 2004

(65) Prior Publication Data

US 2004/0234079 A1 Nov. 25, 2004

(30) Foreign Application Priority Data

Mar. 31, 2003 (CA) .................................. 2424093

(51) Int. Cl.
| H03G 11/00 | (2006.01) |
| H03G 9/00 | (2006.01) |
| H03G 7/00 | (2006.01) |
| H03G 3/00 | (2006.01) |
| H04R 29/00 | (2006.01) |
| H04B 15/00 | (2006.01) |

(52) U.S. Cl. ............................ 381/55; 381/56; 381/102; 381/106; 381/107; 381/104; 381/94.1; 381/94.3; 381/94.7; 381/58

(58) Field of Classification Search ............. 381/55–58, 381/102–106, 94.1, 94.3, 94.7
See application file for complete search history.

(56) References Cited

U.S. PATENT DOCUMENTS

| 5,136,577 A | * | 8/1992 | Amano et al. ................ 370/289 |
| 5,701,352 A | | 12/1997 | Williamson, III |
| 5,745,580 A | * | 4/1998 | Southward et al. ......... 381/71.1 |
| 6,236,731 B1 | * | 5/2001 | Brennan et al. ............. 381/316 |
| 7,003,467 B1 | * | 2/2006 | Smith et al. ................ 704/500 |

* cited by examiner

*Primary Examiner*—Devona E Faulk
(74) *Attorney, Agent, or Firm*—Perman & Green LLP

(57) ABSTRACT

An acoustic shock protection method and device are provided. A pattern analysis-based approach is taken to an input signal to perform feature extraction. A parameter space is identified, which is corresponding to the signal space of the input signal. A rule-based decision approach is taken to the parameter space to detect an acoustic shock event. The device may be advantageously implemented using a weighted overlap-add approach to provide low group delay, high-fidelity and a high degree of protection from acoustic shock events.

31 Claims, 9 Drawing Sheets

METHOD AND SYSTEM FOR ACOUSTIC SHOCK PROTECTION

FIELD OF INVENTION

This invention relates to signal processing technology, and more particularly, to a method and system for acoustic shock protection.

BACKGROUND OF THE INVENTION

Unwanted sounds, such as loud sounds or sounds that have a rapid relative increase in level, may be produced by telephone or radio systems, intentionally or unintentionally. Those sounds are typically experienced by a user through headphones or a headset.

Without protection against those sounds, the user may experience a phenomenon known as acoustic shock. Acoustic shock may result in permanent hearing loss, temporary hearing loss and tinnitus (constant ringing in the ears). Sufferers also report symptoms including extreme pain, vertigo and burning sensations. One of the main issues in the cause of acoustic shock syndrome, apart from the initial high-level sound, is the startle reflex action. This reaction can cause numerous muscles to activate to an unusual degree.

In order to prevent the user from experiencing acoustic shock, the following approaches are provided in telephone systems: 1—Automatic gain control; 2—Adjustable notch filters to remove narrow band tones or "shrieks" when they are detected; 3—Clipping of high level signals using diodes or similar devices:

These approaches have also been combined. All of these approaches use techniques that are well known in the art and have been seen in other application areas (e.g. hearing aids).

The existing devices offer some protection. However, the processed output signal of those devices has reduced fidelity compared to an input signal. Typical distortions of the signal include: "pumping" (unnecessary and audible adjustments of the gain that adversely affect the perceived quality of the processed speech signal) and "holes" (audio dropouts in the processed signal caused by extreme gain adjustments), harmonic distortion as well as the accompanying intermodulation distortion that comes from poor gain control. More complex systems may also suffer from excessive input-output latency (i.e., group delay), which can adversely impact network, acoustic and line echo cancellers.

Currently there are specifications under development that provide guidelines and recommendations for the performance of acoustic shock systems. These include: ITU-T Recommendation P.360 "Efficiency of devices from preventing the occurrence of acoustic pressure by telephone receivers"; UK standard BS6317 specified continuous signals only; US standard, UL1950; EN60950 (http://www.ktl.com/telecoms/shock.htm).

To meet these emerging performance requirements and deliver high-fidelity with low group delay, a new approach is needed. It is, therefore, desirable to provide a new method and system that can fully protect a user against the acoustic shock so as to meet the above guidelines and future guidelines that may emerge.

SUMMARY OF THE INVENTION

It is an object of the invention to provide a novel method and device that obviates or mitigates at least one of the disadvantages of existing systems.

In accordance with an aspect of the present invention, there is provided a method of providing protection against acoustic shock, which includes the steps of: performing a pattern analysis on an input signal to identify a parameter space corresponding to a signal space of the input signal; applying a rule-based decision to the parameter space to detect an acoustic shock event; and removing the acoustic shock event from the input signal to generate a processed output signal.

In accordance with a further aspect of the present invention, there is provided a method of providing protection against acoustic shock, which includes the steps of: performing a weighted overlap-add (WOLA) analysis on an input signal; performing feature extraction on the input signal and performing feature extraction on the plurality of band signals provided by the WOLA analysis; detecting an acoustic shock event based on feature extractions from the input signal and band signals; performing gain control based on the acoustic shock event detection; applying a plurality of calibrated gains to the band signals to reduce the level to meet a predetermined safe level; and performing a WOLA synthesis on the modified band signals (modified by the application of gain) to synthesize an output signal.

In accordance with a further aspect of the present invention, there is provided a system for providing protection against acoustic shock, which includes: an analysis module for performing a pattern analysis on an input signal to identify a parameter space corresponding to a signal space of the input signal; a detection module for applying a rule-based decision to the parameter space to detect an acoustic shock event; and a removal module for removing the acoustic shock event.

In accordance with a further aspect of the present invention, there is provided a system for providing protection against acoustic shock, which includes: a weighted overlap add (WOLA) analysis module for transforming an input signal to a plurality of band signals; a feature extraction module for performing feature extraction on the input signal and for performing feature extraction on the band signals; a detection module for detecting an acoustic shock event based on the feature extractions from the input signal and the band signals; a gain control module for performing gain control based on the shock detection and the extracted features of the input signal and the band signals; and a calibration module for applying calibrated gains to the band signals to reduce the level to meet a predetermined safe level; and a WOLA synthesis module for synthesizing the modified band signals to provide an output signal.

In accordance with a further aspect of the present invention, there is provided a system for providing protection against an acoustic shock, which includes: a weighted overlap-add (WOLA) analysis module for transforming an input signal into a plurality of oversampled sub-band signals in a frequency domain; a processing module for adaptively processing the sub-band signals to remove an acoustic shock event: and a WOLA synthesis module for synthesizing the processed sub-band signals to provide an output signal.

In accordance with a further aspect of the present invention, there is provided an acoustic shock protection method and system, in which a weighted overlap-add (WOLA) filterbank is used and a delay unit is used prior to WOLA analysis enabling predictive features to be fed around the WOLA filterbank analysis stage.

Here, the inherent delay of the WOLA analysis filterbank processing is advantageously used, reducing the necessary amount of added delay while maintaining a low overall group delay. The low group delay of the WOLA filterbank is a considerable advantage.

Other aspects and features of the present invention will be readily apparent to those skilled in the art from a review of the following detailed description of preferred embodiments in conjunction with the accompanying drawings.

BRIEF DESCRIPTION OF THE DRAWINGS

The invention will be further understood from the following description with reference to the drawings in which.

DETAILED DESCRIPTION OF THE PREFERRED EMBODIMENTS

Figure 1:
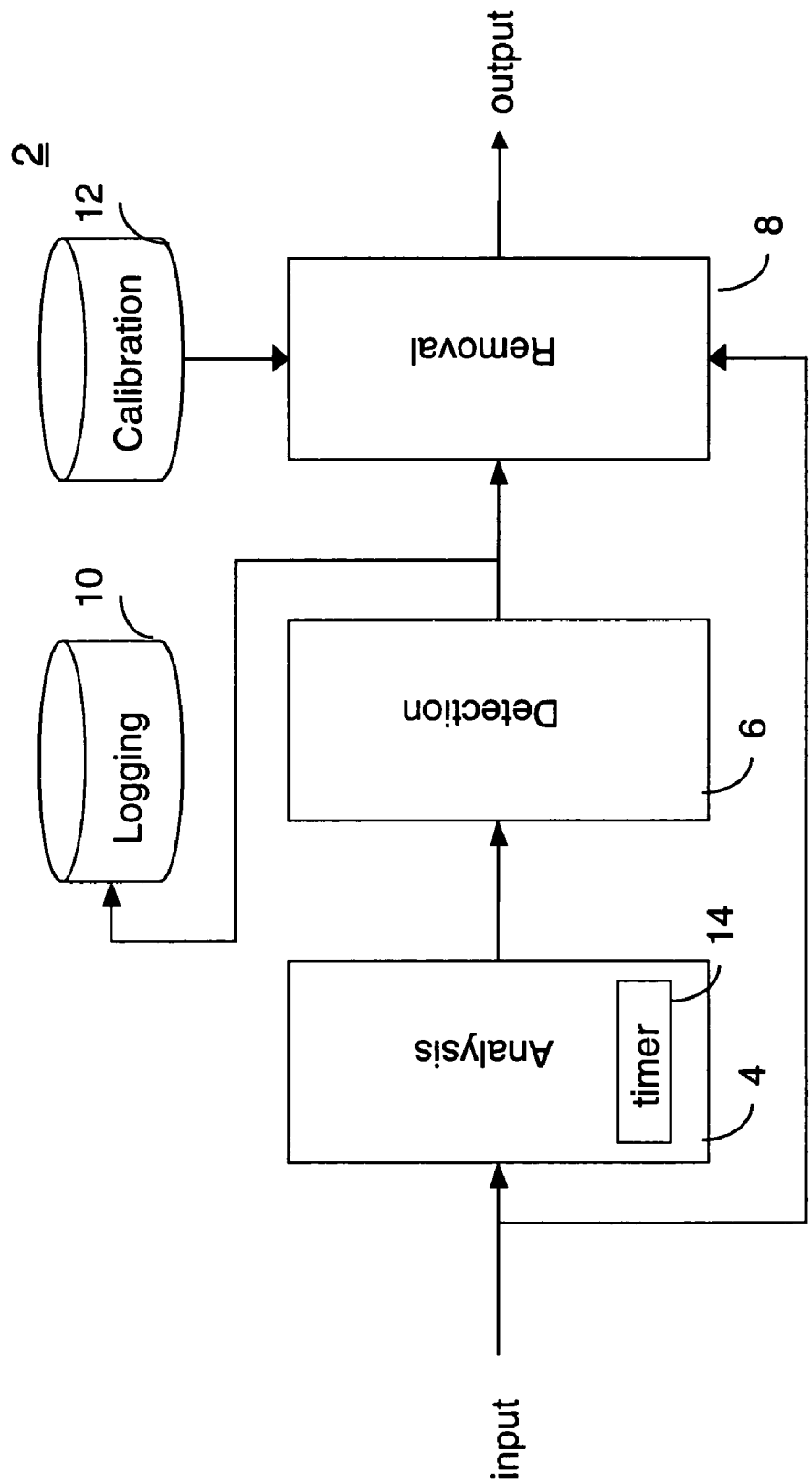
FIG. 1 is a schematic diagram showing an acoustic shock protection system in accordance with an embodiment of the present invention.

FIG. 1 shows an acoustic shock protection system 2 in accordance with an embodiment of the present invention. The acoustic shock protection system 2 includes an analysis block 4, a detection block 6, a removal block 8 and a logging block 10. The system 2 further includes a calibration block 12 that contains data used to calibrate the input and output levels and to support user preferences (e.g. support for personalization). The arrows in FIG. 1 show how these major blocks interconnect and interact with each other.

The acoustic shock protection system 2 implements a pattern analysis-based approach. The approach employs a collection of input signals, referred to as a "signal space", which contains a representative subset of acoustic shock and non-acoustic shock signals that the system will process and, in the case of input signals that contain an acoustic shock event, protect against in typical operation. This signal space is processed via a feature extraction process at the analysis block 4 to realize a reduced dataset representation of the signal space. The collection of reduced dataset representations, one for each of the signals in the signal space, is referred to as a parameter space.

The feature extraction process includes one or more measurements. The pattern analysis-based approach uses the measurements to determine if an acoustic shock is present. The acoustic shocks may include high level, short duration (e.g. a loud sound); level versus time exposure; rapid increase in relative level exposure and/or combination thereof.

The analysis block 4 may use, for example, artificial neural networks, hidden Markov models, Bayesian estimation methods, signal statistics or combinations of signal parameters such as short-term and long-term level over various frequency ranges and time-scales. In some situations, it may be necessary to measure and protect against level versus time exposure to signal levels. In combination with the other subcomponents of the analysis block 4, a timer component 14 in the analysis block 4 provides the capability to protect against level-over-time exposure.

The detection block 6 contains a logical description in terms of inference rules representing patterns of analysis output conditions representing acoustic shock events. The detection block 6, for example, may take the form of a rule-based expert system.

The removal block 8 implements the signal processing necessary to remove the shock event from the input signal, typically by the application of time, level or frequency-dependent gain or a combination thereof, while maintaining the fidelity of the output signal, relative to the input signal.

The logging block 10 implements on-line data collection of the key parameters of shock events. This information is time-stamped using the timer 14 or another similar means and may be categorized to provide accurate data records for later downloading and analysis.

The calibration block 12 provides data that is required to account for the acoustic and electrical differences between various headphones, headsets, systems and other components. The data from the block 12 ensures that the output level experienced by the user of the system 2 does not exceed a preset maximum as a function of time and frequency. The preset maximum may be changeable for each user. The logging block 10 and the calibration block 12 may be detachably attached to the system 2.

In FIG. 1, the analysis block 4, the detection block 6 and the removal block 8 are shown separately. However, the component of the analysis block 4 may be used as the component of the detection block 6 or the removal block 8. The component of the detection block 6 may be used as the component of the removal block 8. Processing done in each of the blocks may be reused in other blocks to minimize the computational and memory requirements for implementing the invention.

For example, the system 2 may re-use some of the features, which are used during analysis, as information (e.g. level measurements) to perform gain control in the removal block 8. The measurements used to perform analysis and detection at the analysis block 4 and the detection block 6 are reused to perform the signal processing necessary for acoustic shock removal. Similarly, these measurements can be used as a portion of the data collected by the logging block 10.

The pattern analysis-based approach in the acoustic shock protection system 2 also provides the flexibility to effectively deal with a wide range of input signal types. This identification mechanism/method effectively makes use of various signal parameters to identify acoustic shock events.

A feedforward configuration is used to provide fast-acting and intelligent gain control. In a preferred embodiment, the gain applied to the processed signal is controlled by a set of gain control rules that receive, as input, the output(s) from the pattern analysis. While gain control is highly useful in removing acoustic shock when only a single signal is available, the addition of adaptive filtering provides further performance for periodic signal disturbance sources or in applications where a secondary input is available. The gain application and adaptive filtering blocks are seen as complementary. The gain control block acts quickly to remove acoustic shock transients. In cases where the shock is periodic noise or predictable from a secondary input, the adaptive filtering block converges to remove this noise. The details of the adaptive filtering block will be presented later; for now, the discussion will assume only a single input is available.

The entire implementation is parameterizable. This allows the flexibility needed to deal with a wide range of environments and acoustic configurations.

Figure 2:
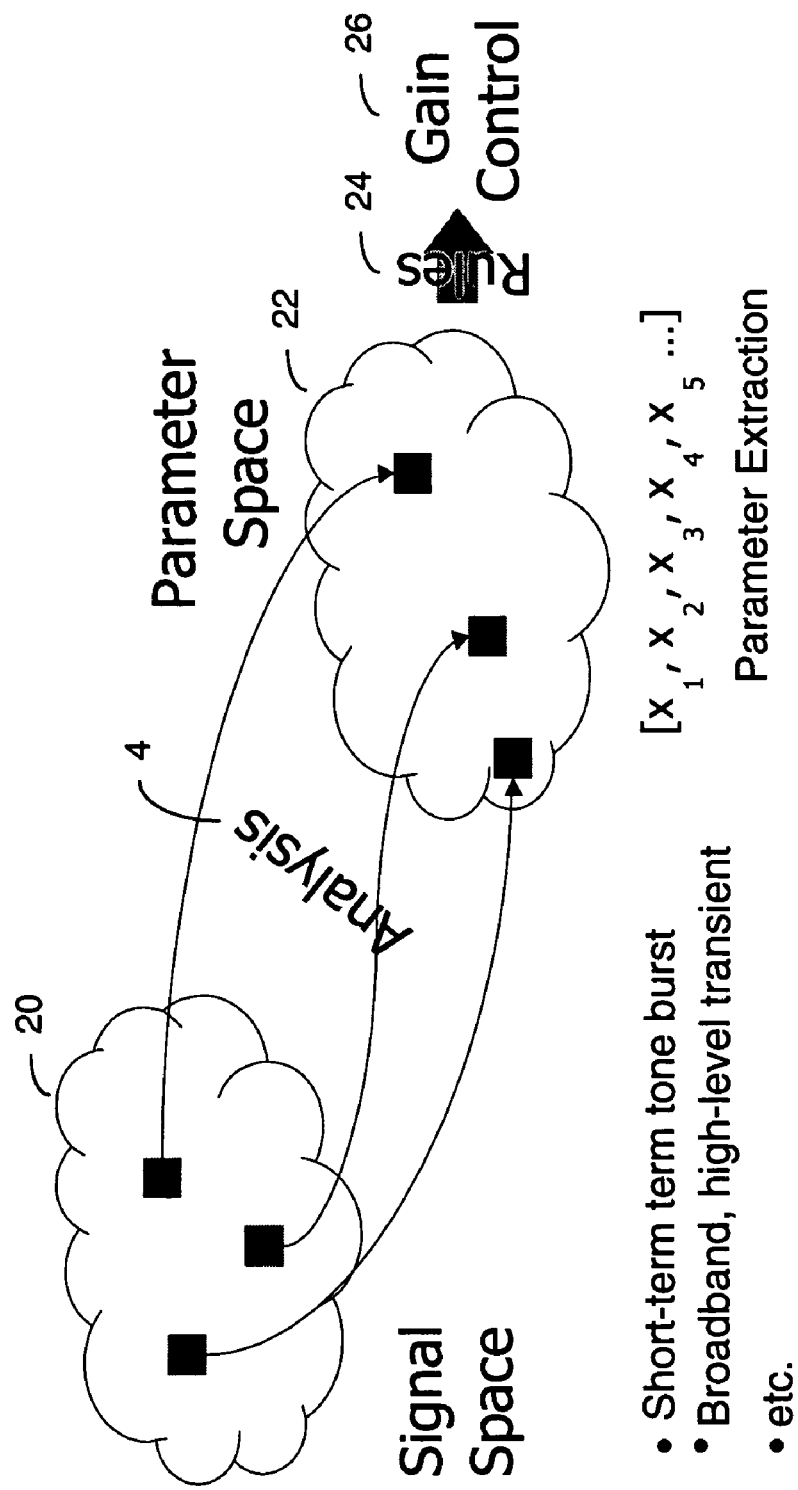
FIG. 2 is a schematic diagram showing the process of FIG. 1.

FIG. 2 is a schematic diagram showing the signal processing for the system in FIG. 1. Referring to FIGS. 1 and 2, a signal space 20 is mapped to a parameter space 22 defined by [X1, X2, X3, X4, X5 . . . ], by performing the feature extraction at the analysis block 4 of FIG. 1. The detection block 6 makes a rule-based decision (rules 24) regarding the presence or absence of an acoustic shock event using the parameters. Then, the removal block 8 of FIG. 1 performs gain control 26 to remove the acoustic shock event.

This approach allows the system 2 to be flexible and trainable. The signal space 20 can always be extended to account for a signal class or type for which protection must be provided. The rules 24 used for the gain control 26 can be adjusted to meet new requirements. Preferably, the rules 24 are implemented and adjusted in software or firmware.

In one embodiment, an oversampled filterbank, such as a weighted overlap-add (WOLA) filterbank, is applicable to the pattern analysis-based approach of acoustic shock detection. The WOLA filterbank is described in U.S. Pat. No. 6,236,731, "Filterbank Structure and Method for Filtering and Separating an Information Signal into Different Bands, Particularly for Audio Signal in Hearing Aids" by R. Brennan and T. Schneider, issued on May 22, 2001, and U.S. Pat. No. 6,240,192, "Apparatus for and method of filtering in an digital hearing aid, including an application specific integrated circuit and a programmable digital signal processor" by R. Brennan and T. Schneider, issued on May 29, 2001, which are incorporated herein by reference.

The WOLA filterbank includes a WOLA analysis filterbank and a WOLA synthesis filterbank. The WOLA analysis filterbank receives a plurality of information signals in the time domain and transforms the information signals into a plurality of band signals in the transform (frequency) domain. The WOLA synthesis filterbank receives a plurality of band signals in the transform (frequency) domain and transforms the band signals into a single information signal in the time domain. A data processor for processing the output of the WOLA analysis filter bank may be provided between the WOLA analysis filterbank and the WOLA synthesis filterbank.

Figure 3:
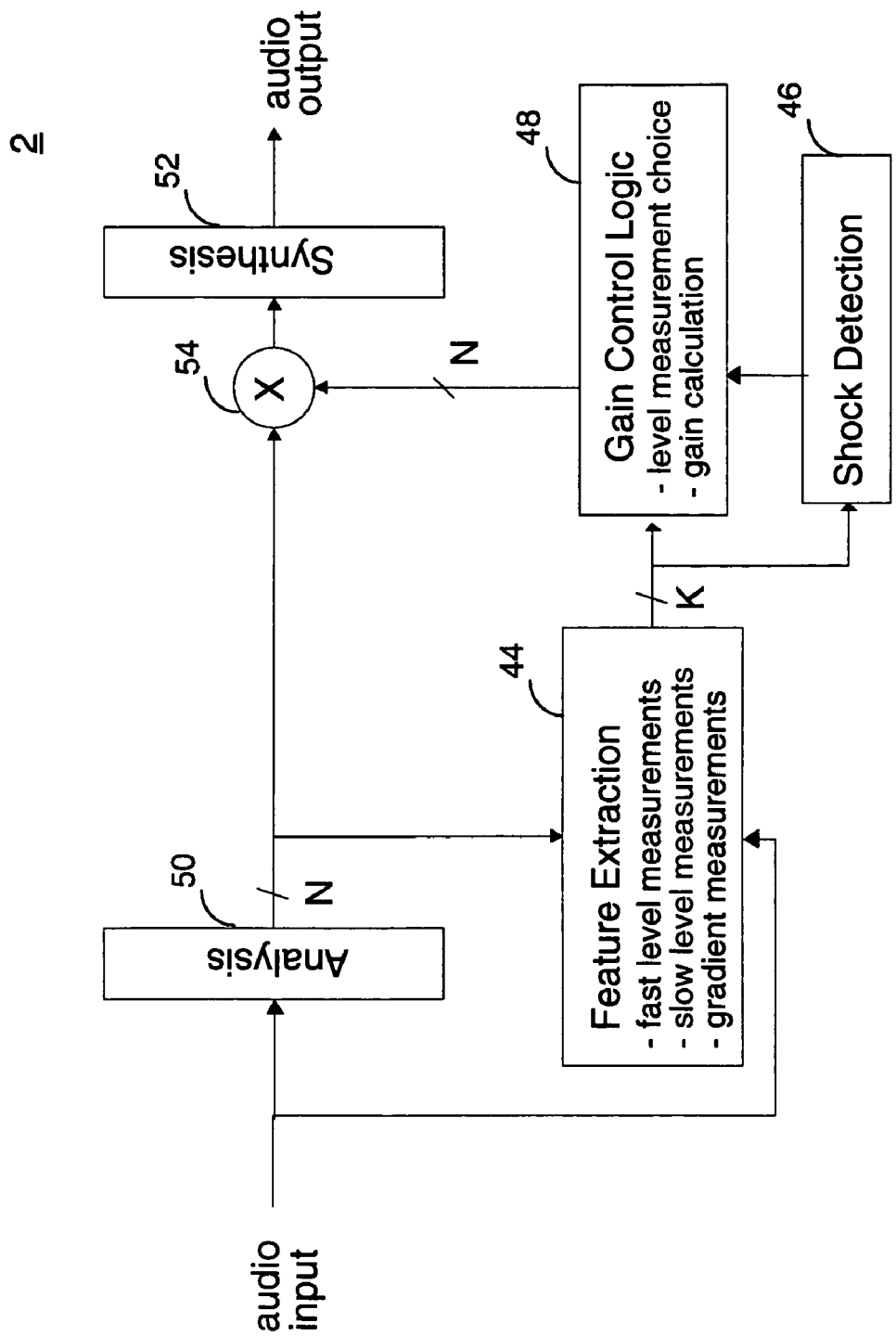
FIG. 3 is a schematic diagram showing one example of the acoustic shock protection system of FIG. 1, which has a WOLA filterbank.

FIG. 3 shows one example of the acoustic shock protection system 2 of FIG. 1. The acoustic shock protection system 2 of FIG. 3 includes a feature extraction block 44, a shock detection block 46, a gain control logic block 48, a WOLA analysis filterbank 50, a WOLA synthesis 52 and a complex multiplier 54. The WOLA analysis filterbank 50 and the feature extraction block 44 correspond to the analysis block 4 of FIG. 1. The shock detection block 46 corresponds to the detection block 6 of FIG. 1. The gain control logic block 48 corresponds to the removal block 8 of FIG. 1.

The feature extraction block 44 performs level measurements. For example, the level measurements include fast level measurement, slow level measurement, gradient measurement, broadband measurement in the time-domain and narrowband measurement in the filterbank bands or groups of bands. The gain control logic block 48 selects appropriate level measurements and performs gain calculations.

The WOLA analysis filterbank 50 of the WOLA filterbank is used to divide the input signal into a plurality of frequency bands. These bands and the raw input signal are then processed individually or in combination to extract relevant signal features in the feature extraction block 44. This combination of processing steps is implemented at the analysis block 4 of FIG. 1. The results of the feature extraction are then passed to the shock detection block 46. The shock detection block 46 makes a rule-based decision about the presence or absence of an acoustic shock event. The shock detection block 46 performs the role of the detection block 6 of FIG. 1. The shock detection decision is then used in conjunction with the extracted features to perform intelligent gain control at the gain control logic block 48.

The gain control logic block 48 has inputs from both the feature extraction 44 and the shock detection block 46. For example, the gain control logic block 48 may implement gain control logic using static gain curves in each sub-band or by applying a gain calculated from the raw input signal level, or by a combination of the two. The application of the gain to these bands provides the control required to implement acoustic shock protection. The complex-multiplier 54 (used in real mode in this application) multiplies the output of the WOLA analysis filterbank 50 and the output of the gain control logic block 48. The WOLA synthesis block 52 of the WOLA filterbank receives the outputs of the multiplier 54 and transforms them into audio output in the time domain.

The acoustic shock protection system with the WOLA filterbank provides high fidelity and low group delay. It also provides high adjacent band isolation that permits high-fidelity removal of frequency isolated shock events, such as tones or other narrow band signals. This implementation can be advantageously realized on the system architecture disclosed in U.S. Pat. No. 6,236,731 and U.S. Pat. No. 6,240,192.

Figure 4:
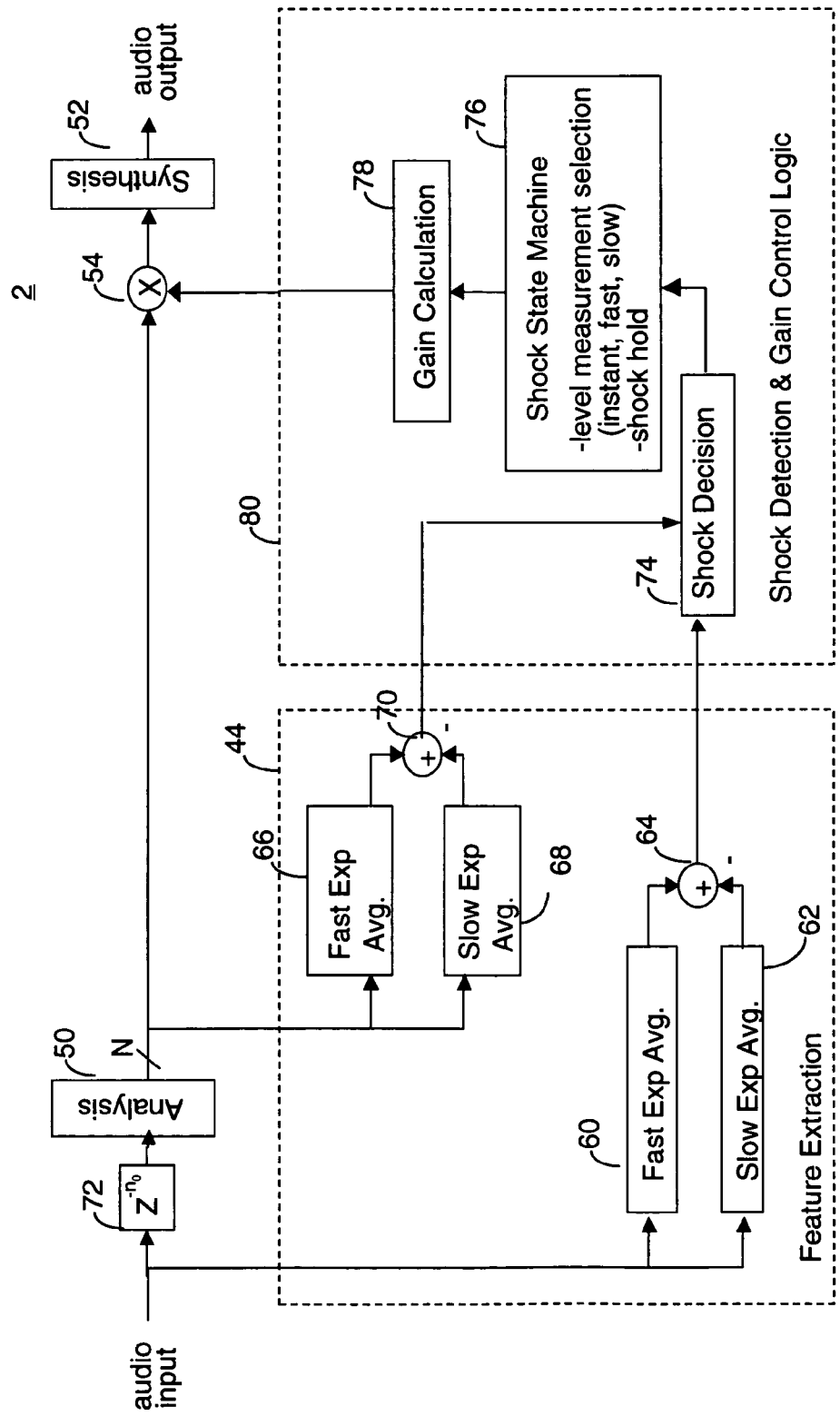
FIG. 4 is a schematic diagram showing one example of the WOLA based architecture of FIG. 3.

FIG. 4 shows one example of the feature extraction block 44, the shock detection block 46 and the gain control logic block 48 of FIG. 3.

The feature extraction block 44 of FIG. 4 employs time-domain (pre-analysis) and frequency-domain (post-analysis) measurements. The feature extraction block 44 of FIG. 4 includes fast and slow time-domain broadband level measurements and a vector of fast and slow narrowband level measurements corresponding to each frequency band.

The time domain measurements are now described in detail. In FIG. 4, a fast exponential average block ("Fast Exp. Avg.") 60, a slow exponential average block ("Slow Exp Avg.") 62 and a summer 64 implements the time domain measurements.

The time domain measurements can be first-order fast and slow exponential averages of the RMS (root mean square) signal level that are well-known in the art. However, other level measurement techniques, such as short or long term minimum and maximum signal levels, order statistics (e.g., median), outputs from distribution measurements (e.g., the level that represents the $95^{th}$ percentile) or other similar measurements well known in the art may be applicable.

The difference between these levels is a feature, which is sent to the shock decision block 74. Furthermore, these levels are calculated ahead of the WOLA processed signal using a delay block 72 ("$Z^{-n_0}$" in FIG. 4) that provides a time delay corresponding to $n_0$ samples. This delay permits the time-domain measurements to indicate the presence of a high level (and a potential acoustic shock event) to the shock detection rules before the shock appears in the plurality of outputs from the analysis operation. A fundamental property at the onset of any large acoustic transient or shock is that it is initially indistinguishable from a broadband disturbance. Only later, as the shock progresses through the analysis filterbank, is further classification possible indicating the presence of narrowband/tonal noise or broadband noise. A rapid increase in time-domain energy, therefore, indicates that some form of shock condition is initiating and signals that a sensitization of the frequency domain detectors located in the frequency bands after the analysis stage should occur. This sensitization allows the gain logic to preemptively adapt eliminating a possible, brief high-level transient at the onset of a high level, because the gain control has already "seen" the high-level and had, if necessary, reduced the relevant gain or gains accordingly. The WOLA analysis filterbank 50 processes the output of the delay block 72. This parameterizable feed-forward delay allows the measurements to indicate the presence of shock one or more processing blocks before the shock would be (if unmodified) experienced by the end user, thereby improving protection. The inherent group delay of the WOLA analysis is used advantageously to reduce the delay time no implemented by the delay unit 72, in some instantances permitting the delay no to be reduced to zero with the WOLA analysis used to provide all of the required delay.

The frequency domain measurements are now described in detail. In FIG. 4, a fast exponential average block ("Fast Exp. Avg.") 66, a slow exponential average block ("Slow Exp Avg.") 68 and a summer 70 implement the frequency domain measurements.

The frequency domain measurements can also be fast and slow exponential averages of the RMS signal level in each frequency band (as are well-known in the art). Other level measurement techniques, such as short or long term minimum and maximum signal levels, order statistics (e.g., median), outputs from distribution measurements (e.g., the level that represents the 95$^{th}$ percentile) or other similar measurements well known in the art are also possible. The difference or other comparative measurement between these levels is a feature, which is sent to the shock decision block 74.

The blocks 60 and 62 may act as a dual time-constant detector, which have averaging filters and detect current signal levels in accordance with the following equations (1) to (3):

$$L(i) = 20\log\left(\frac{\sqrt{\frac{1}{R}\sum_{j=1}^{R} X_j^2}}{\text{CALIB\_LEVEL}}\right) \quad (1)$$

$$L_{fast}(i) = \alpha_{fast}L(i) + (1-\alpha_{fast})L_{fast}(i-1) \quad (2)$$

$$L_{slow}(i) = \alpha_{slow}L(i) + (1-\alpha_{slow})L_{slow}(i-1) \quad (3)$$

Where L(i) indicates the level measurements of the i$^{th}$ block;

α is a time constant determined from the desired filter time constants;

R is the block size used for WOLA analysis;

$X_j$ are the block samples;

CALIB_LEVEL is a calibration level chosen during configuration;

the subscripts of "fast" and "slow" indicate the fast and slow filters respectively.

This detector computes exponentially averaged level measurements using a fast time constant and a slow time constant. The dual time-constant detector extracts current signal levels through the two measurements and detects the presence of relatively loud transients through the difference between the two measurements. The detector operates in dB levels but may also operate on non-logarithmic power measurements. Using dB levels, the difference is the ratio of the power measurements in each filter.

Similarly, the blocks 66 and 68 may act as a dual time-constant detector for each sub-band, which detect current signal levels in accordance with the following equations (4) to (6):

$$L_j(i) = 20\log\left(\frac{|X_j|}{\text{CALIB\_LEVEL}}\right) \quad (4)$$

$$L_j^{fast}(i) = \alpha_j^{fast}L_j(i) + (1-\alpha_j^{fast})L_j^{fast}(i-1) \quad (5)$$

$$L_j^{slow}(i) = \alpha_j^{slow}L_j(i) + (1-\alpha_j^{slow})L_j^{slow}(i-1) \quad (6)$$

Where $L_j(i)$ indicates the level measurements of the i-th block in the j-th band;

$X_j$ is the current complex measurement in the j-th band;

α is a time constant for that band's filter;

the superscripts of "fast" and "slow" indicate the fast and slow filters respectively.

These detectors provide information about the presence of narrowband shock conditions to the shock detection rules. These detectors operate in dB levels but may also operate on non-logarithmic power measurements. Using dB levels, the difference is the ratio of the power measurements in each filter.

The shock detection and gain control logic 80 of FIG. 4 is now described in detail. The shock detection and gain control logic 80 includes the shock decision block 74, a shock state machine 76 and a gain control block 78. The shock detection and gain control logic 80 corresponds to the shock detection block 46 and gain control logic 48 of FIG. 3.

The shock decision block 74 of FIG. 4 makes a decision about the presence of acoustic shock at both the broadband and narrowband levels. A large value in either the time-domain feature or the band-level features indicates a quick increase in relative sound exposure level for the end user. The thresholds may be set by experimentation and heuristics. Alternatively, these could be set using automatic training methodologies such as artificial neural networks.

The decision at the shock decision block 74 is then used by a shock state machine 76, which uses a rule-base to decide whether the current exposure level is a potentially harmful acoustic shock event. The shock state machine 76 coupled with the shock decision block 74 corresponds to the detection block 6 of FIG. 1.

Figure 5:
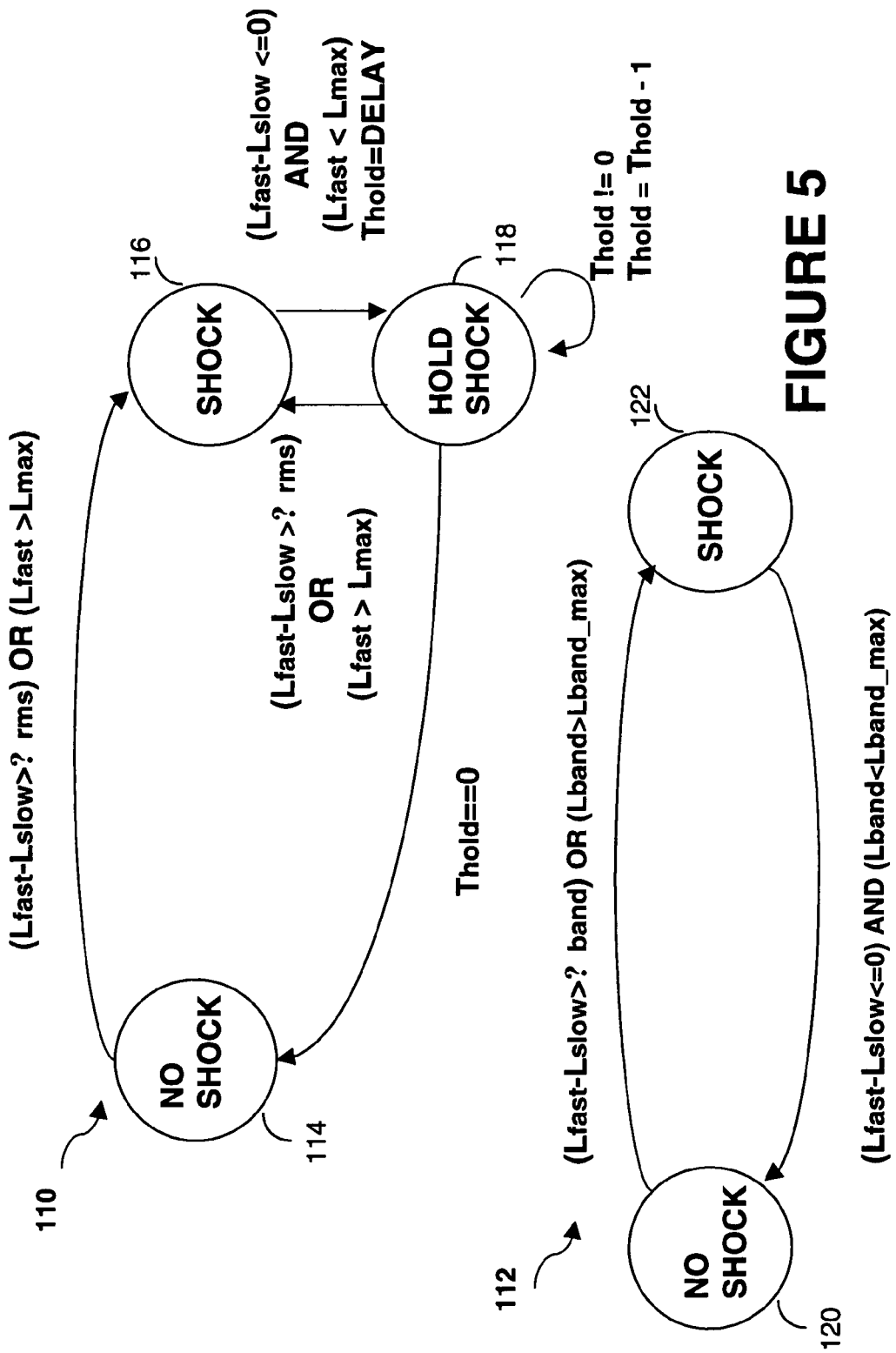
FIG. 5 is a schematic diagram showing one example of the shock state machine of FIG. 4.

For example, the shock detection block 46 outputs a flag, such as yes/no flag, for overall shock and a flag, such as yes/no flag, for shock within each sub-band. The overall shock flag is used internally for the shock detection. The sub-band shock flag is used for gain calculation. FIG. 5 shows one example of the shock state machine 76 of FIG. 4. The shock state machine 76 of FIG. 5 contains a overall shock state machine 110 and a band shock state machine 112. The overall shock state machine 110 examines a difference between the time-domain level measurements to determine a current condition, i.e., "no shock" state 114, "shock" state 116 or "hold shock" state 118. The "hold shock" state compensates for the feedforward delay 72 so that an overall shock condition is not prematurely terminated before the input signal has reached the plurality of output bands from WOLA analysis block 50. The band shock state machine 112 examines a difference between the sub-band level measurements to determine a current condition, i.e., "no shock" state 120 or "shock" state 122.

In FIG. 5, $\Delta_{rms}$ represents a parameterizable threshold in time-domain, and $\Delta_{band}$ represents a parameterizable threshold in sub-band domain. The general condition for shock is either a time-domain level difference greater than the threshold $\Delta_{rms}$, or a sub-band level difference greater than the threshold $\Delta_{band}$.

Shock is also automatically asserted when the fast level measurements exceed specified maximum level thresholds labeled $L_{max}$ for the time-domain level and $L_{band-max}$ for the sub-band level measurements. Shock is exited only when the maximum level threshold is no longer exceeded and the measurement difference has dropped back to zero or less. The maximum thresholds deal with the case of absolute shock, where the level is higher than the tolerated output. The difference thresholds deal with the case of relative shock, where the average level of the signal has increased drastically in a short period of time and could be shocking. In addition to these level based transition guards, there is also a hold time $T_{hold}$ and the hold shock state 118 associated with the overall shock state. This is to compensate for the time domain measurement "look-ahead" caused by the digital delay. The hold time $T_{hold}$ is configureable, and is greater than or equal to the delay parameter ($n_0$) divided by the WOLA analysis block size (R).

Referring to FIG. 4, the acoustic shock state, i.e. whether acoustic shock is currently occurring or not, is then used by the gain control logic at gain calculation block 78 of FIG. 4. The gain calculation block 78 corresponds to the removal block 8 of FIG. 1.

The output of the shock decision can be used in the logging portion (e.g. block 10 of FIG. 1).

The detector 6 of FIG. 1, 46 of FIG. 3 and 74/76 of FIG. 4 may use fuzzy logic, neural networks and/or combinations of overall-level and band-level control. Preferably, the frequency-domain processing is implemented with delay 72 of FIG. 4 before the WOLA analysis filterbank 50, with the inherent WOLA delay being sufficient to encompass the entire delay time needed in some applications, to obtain look-ahead functionality.

Figure 6:
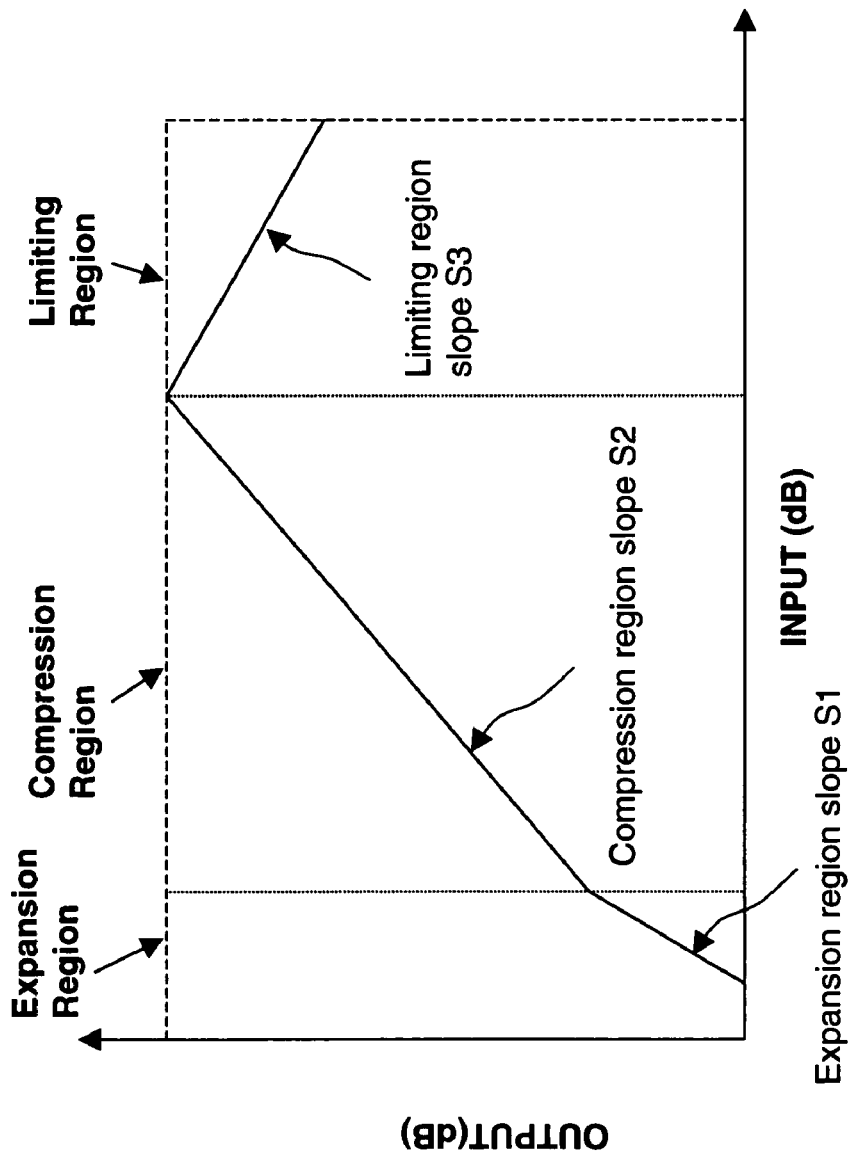
FIG. 6 is a schematic diagram showing one example of an input-output function of the gain control of FIG. 4.

In one embodiment, the gain calculation block 78 employs a gain control using static input-output (IO) curves for each sub-band. By using a separate IO curve for each sub-band, frequency dependent level limiting can be achieved. The input-output behavior is implemented internally by the algorithm as an input-gain function. FIG. 6 shows one example of the IO function of the gain control. The entire curve is specified by the expansion region slop S1, the compression region slop S2, the limiting region slop S3 and the co-ordinates of the two knee-points, which implicitly sets the compression ratio. Calibration for input and output analog responses can be taken into account by adjusting the gain applied accordingly so that the desired IO curve is achieved.

The choice of what input level to use during the gain control is controlled by the output of the shock state machine 76. During a "shock" condition, peak instantaneous levels are tracked and used for the gain calculations. Using the instantaneous levels ensures that the shock is suppressed immediately and tracking a peak ensures that the gain is steady during an instance of acoustic shock, thereby improving fidelity.

Output gain is reduced in bands where acoustic shock is detected in order to protect the user. The fast and slow level measurements from the feature extraction block, combined with instantaneous levels are used to compute the desired gain. Confining the output attenuation to only the bands where shock is prevalent minimizes any distortion of the output and thus provides improved fidelity.

These gain control details, such as maximum output level, and shock decision thresholds constitute the parameters that are available for personalization and calibration (e.g. block 12 of FIG. 1).

Figure 7:
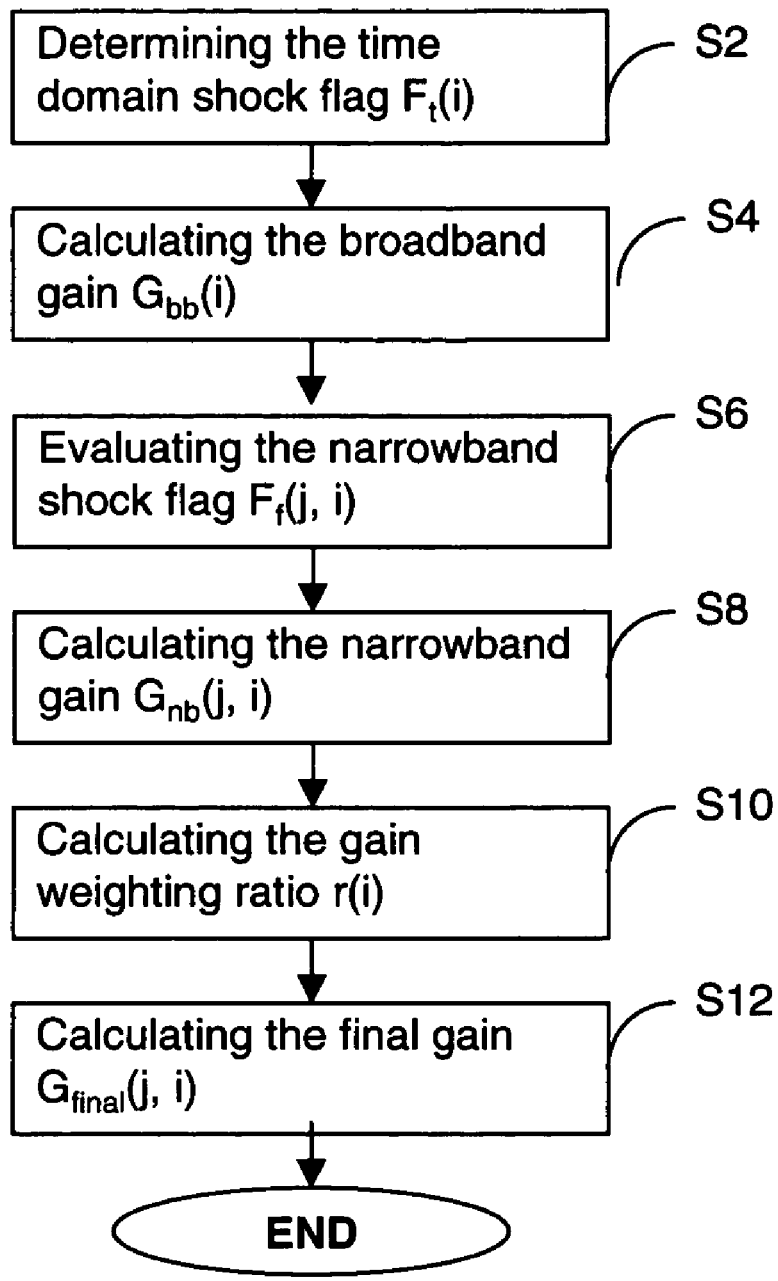
FIG. 7 is a flow chart showing one example of implementing gain calculation at the gain calculation block of FIG. 4.

In another embodiment, the gain calculation block 78 performs gain calculation as shown in FIG. 7. FIG. 7 shows one example of the gain calculation at the gain calculation block 78. In step S2, the time domain shock flag $F_t(i)$ for the given $i^{th}$ input block is determined based on the measurements of $L_{fast}(i)$ and $L_{slow}(i)$. In step S4, a broadband gain $G_{bb}(i)$ for the $i^{th}$ block (i.e. block i) is calculated in response to the time domain shock flag $F_t(i)$. In step S6, a narrowband shock flag $F_f(j,i)$ for band j, block i is evaluated. In step S8, a narrowband gain $G_{nb}(j,i)$ for the band j, block i is calculated in response to the narrowband shock flag $F_f(j,i)$. In step S10, a gain weighting ratio r(i) for the block i is calculated. In step S12, a final gain $G_{final}(j, i)$ is calculated using the gain weighting ratio r(i).

The calculation of the broadband gain $G_{bb}(i)$ is described in detail. At the beginning of the shock, which is detected in the time domain ($F_t(i)=1$), a broadband counter $n_{bb}$ is set to count down the number of frames which are affected only by the broadband gain for reducing the transient effect. This number can be a fixed value, or is configurable as an adaptive value. The broadband gain $G_{bb}(i)$ is calculated based on the time domain shock flag $F_t(i)$ and the broadband counter $n_{bb}$ in accordance with the equation (7):

$$\begin{cases} G_{bb}(i) = 0 & \text{if } F_t(i) = 0 \\ G_{bb}(i) = L_{inst}(i) - T_{bb} & \text{if } (F_t(i) = 1 \wedge n_{bb}(i) > 0) \\ G_{bb}(i) = L_{avg}(i) - T_{bb} & \text{if } (F_t(i) = 1 \wedge n_{bb}(i) \leq 0) \end{cases} \quad (7)$$

where $L_{inst}(i)$ and $L_{avg}(i)$ are the instantaneous and fast average energy levels of the input block, respectively; and $T_{bb}$ is a broadband threshold, which is configurable. A user can determine the threshold value $T_{bb}$ by calibrating the system for limiting the output to certain dB SPL (Sound Pressure Level) value.

Initially the time domain shock flag $F_t(i)$ is checked to determine the occurrence of a shock. If $F_t(i)$ is zero, i.e. no shock, the broadband gain $G_b(i)$ is set to 0 dB, to not affect the incoming signal in normal situations. If $F_t(i)$ is equal to one, the signal is carrying a shock and the broadband gain has to be calculated as the difference between the energy level and the time domain threshold value. At this point, the energy level has to be chosen based on the position of the processed block relative to the beginning of the shock. This is due to the transient reduction function. The transient reduction function applies only the broadband gain at the beginning of the transient time when the shock is detected only in time domain. Therefore, to compress the shock fully during the transient time, it is required to use instantaneous energy level for the given block. Since the broadband counter $n_{bb}$ represents the count down for the duration of the transient effect, the instantaneous energy level $L_{avg}(i)$ is used for the blocks with $n_{bb}$ greater than zero, otherwise, for minimizing the fluctuation on the gain values, the average energy level $L_{avg}(i)$ is used to calculated the gain.

The narrowband shock flag $F_f(j,i)$ is detected using the shock state machine as described in FIG. 5. The computation of the narrowband gain $G_{nb}(j,i)$ is described in detail. The narrowband gain $G_{nb}(j,i)$ is calculated based on the status of the frequency domain shock flag $F_f(j,i)$ in accordance with the equation (8) where j is the band index and i is the input block number. If there is no shock detected in the band i ($F_f(j,i)=0$), the narrowband gain $G_{nb}(j,i)$ is set to 0 dB, otherwise, the gain $G_{nb}(j,i)$ is calculated as the difference between the energy level of the band and its corresponding threshold value $T_{nb}(j)$. At this point, similar to the broadband gain, the instantaneous energy level $L_{inst}(j, i)$ is used to calculate the gain when the input block is during the transient time (i.e. $n_{bb}$ is greater than zero), and the average energy level $L_{avg}(i)$ is applied if the input block is after the transient time (i.e. $n_{bb}$ is equal to zero). This ensures that the shock is fully compensated during the transient time and the gain variations are minimized during the shock and after the transient time:

$$\begin{cases} G_{nb}(j,i) = 0 & \text{if } F_f(j,i) = 0 \\ G_{nb}(j,i) = L_{inst}(j,i) - T_{nb}(j) & \text{if } (F_f(j,i) = 1 \wedge n_{bb}(i) > 0) \\ G_{nb}(j,i) = L_{avg}(j,i) - T_{nb}(j) & \text{if } (F_f(j,i) = 1 \wedge n_{bb}(i) \leq 0) \end{cases} \quad (8)$$

The calculation of the gain weighting ratio r(i) is now described in detail. The gain weighting ratio r(i) is a key parameter for calculating the appropriate gain value for each band. It defines the amount of contribution made by the broadband gain and narrowband gain to the final gain value, based on the time domain and frequency domain shock states. The equation (9) represents the conditions used to calculate the gain weighting ratio r(i):

$$\begin{cases} r(i) = 1 & \text{if } \{F_t(i) = 0\} \\ r(i) = 0 & \text{if } \{F_t(i) = 1 \wedge (\exists F_f(1:N,i) = 0)\} \\ r(i) = 10^{[L_{max}(i) - L_{total}(i)]} & \text{if } \{F_t(i) = 1 \wedge (\exists F_f(1:N,i) = 1)\} \end{cases} \quad (9)$$

where N is the number of the bands; and $L_{total}(i)$ is the sum of the energy levels of all the bands evaluated for the input block i:

$$L_{total}(i) = \sum_{n=1}^{N} 10^{L_{inst}(n,i)}$$

The value r(i) is calculated per sample block and it considers the overall frequency domain shock flag to be equal to one when at least one band is in shock.

The value r(i) is set to one during the normal conditions where no shock is detected (i.e. $F_t(i)=0$ and $\forall F_f(1:N,i)=0$) and also at the end of a shock (i.e. $F_t(i)=0$ and $\forall F_f(1:N,i)=1$). This is due to the fact that by setting the gain ratio to one during the normal conditions, only the narrowband gain is enabled and by changing the gain values, the frequency response of the system can be modified. Also, at the end of a shock, because of the "inherited blocks" from the shock period in the analysis window, the frequency bands carry high energy levels while no time domain shock has been detected. This results in an overshoot in the synthesis output if no gain is applied. This effect can be managed by enabling the narrowband gain and using the average energy band levels $L_{avg}(j,i)$ to calculate the gain values.

During the transient time, initially, the shock is detected only in the time domain (i.e. $F_t(i)=1$ and $\forall F_f(1:N,i)=0$) and as a result only the broadband gain can be used to compress the shock. Therefore for full shock compensation, the gain ratio is set to zero. The narrowband gain is brought to the picture automatically, as soon as the band levels reach the threshold values.

During the steady state of the shock Oust after the transient and before the end), the r(i) is calculated as the ratio of the maximum energy level carried by any of the bands in block i ($L_{max}(i)=Max(L_{inst}(1:N,i))$), over the total energy carried by all the bands in corresponding block, $L_{total}(i)$. By having this value as the gain ratio, the concentration of energy over the spectrum is calculated and the energy of a band is reduced based on its contribution to the total energy level. In spite of the fact that this values is the same for all the bands, the final gains are still customized for the bands in shock based on their narrowband gains.

The calculation of the final gain $G_{final}(j,i)$ is now described in detail. The final gain for each band j, is calculated in accordance with the equation (10):

$$\begin{cases} G_{final}(j,i) = r(i)G_{nb}(j,i) + (1-r(i))G_{bb}(i) & \text{if } F_f(j,i) = 1 \\ G_{final}(j,i) = (1-r(i))G_{bb}(i) & \text{if } F_f(j,i) = 0 \end{cases} \quad (10)$$

According to an aspect of the present invention, processing in a plurality of frequency domain bands provides the flexibility needed to effectively protect against wideband (in frequency) and narrowband shock signals. For narrowband signals (e.g. tones or dual-tones), band-based gain control and/or adaptive processing provides localized gain control that results in high fidelity because gain adjustments are only made in the frequency ranges where they are necessary.

Periodic acoustic shock signals can be virtually eliminated using sub-band implementations of Least Mean Squares (LMS) periodic interference cancellation techniques as described in, for example, B. Widrow and S. D. Stearns, "Adaptive signal processing." Englewood Cliffs, N.J.: Prentice-Hall, 1985., which is incorporated herein by reference. These may be implemented at the block 8 of FIG. 1 in sub-band outputs from the WOLA analysis as described below.

Sub-band adaptive processing disclosed in Canadian Patent Application No. 2,397,080, entitled by "Sub-band Adaptive Signal Processing In An Oversampled Filterbank" and Canadian Patent Application No. 2,437,477, entitled by "Method and System for Processing Subband Signals Using Adaptive Filters", which are incorporated by reference herewith, is applicable to the sub-band processing of the present invention.

Figure 8:
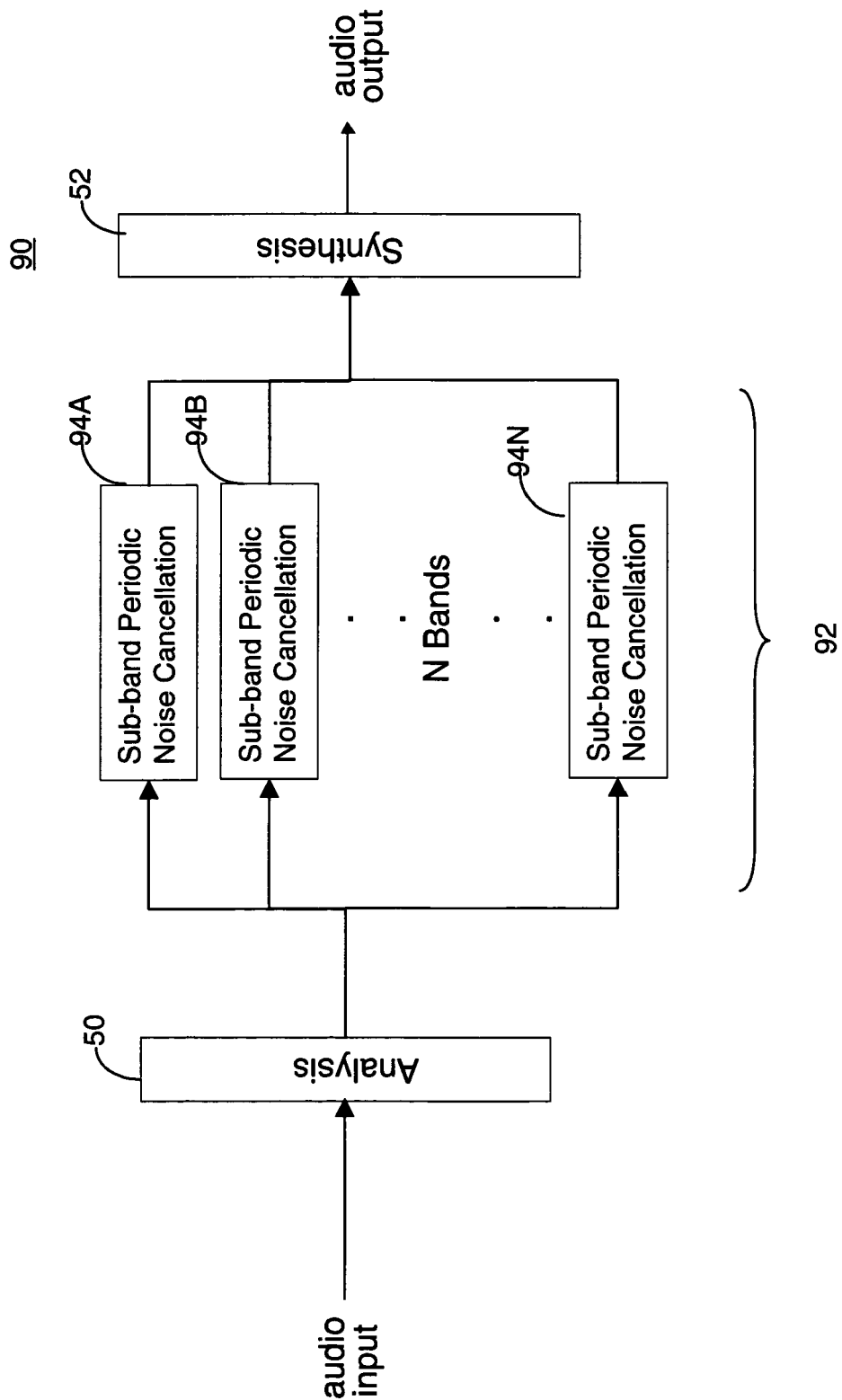
FIG. 8 is a block diagram showing a sub-band adaptive periodic noise cancellation technique in accordance with another embodiment of the present invention.

FIG. 8 shows an acoustic shock protection system 90 in accordance with another embodiment of the present invention. The audio signal contains the desired speech and acoustic shock event that is assumed to be a periodic noise source. The acoustic shock protection system 90 employs sub-band adaptive periodic noise cancellation technique and acts as a periodic noise canceller.

The system 90 of FIG. 8 includes the WOLA analysis filterbank 50, the WOLA synthesis filterbank 52 and a processing block 92. The processing block 92 includes a plurality of sub-band periodic noise cancellation blocks 94A-94N, which corresponds to N sub-bands. The WOLA analysis filterbank 50 transforms audio input into a plurality of sub-bands. Each sub-band is then passed to the corresponding periodic noise cancellation block. The WOLA synthesis filterbank 52 combines the outputs of the processing block 92 into a single signal.

The system of FIG. 2 may further contain the sub-band periodic noise cancellation block of FIG. 8 to improve acoustic shock cancellation. As described above, the system of FIG. 2 works quickly to remove the acoustical trauma while the sub-band periodic noise cancellation goes a step further to actually cancel the interference whenever a periodic acoustical shock is present.

Figure 9:
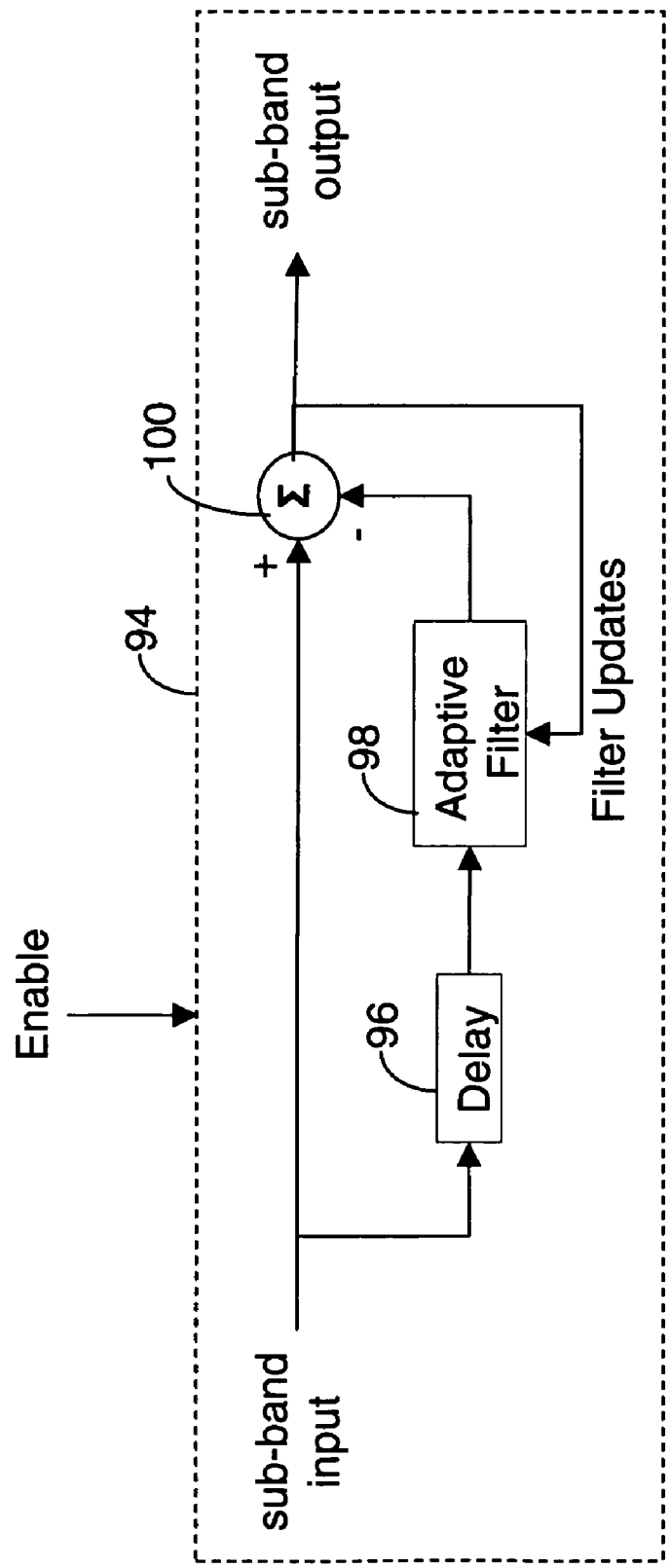
FIG. 9 is a schematic diagram showing one example of the sub-band periodic noise cancellation block of FIG. 8.

FIG. 9 shows one example of the sub-band periodic noise cancellation block 94 of FIG. 8. The sub-band periodic noise cancellation block 94 includes a delay block 96, an adaptive filter 98 and a summing block 100.

A sub-band input is delayed at the delay block 96. The delayed version of the audio sub-band input is filtered by the adaptive filter 98 and then subtracted from the original subband input by the block 100. The resulting error signal from the block 100 acts as the sub-band output. The sub-band output is also applied to the adaptive filter 98 to update the adaptive filter 98 using the LMS algorithm or other similar techniques. The adaptive filter 98 will cancel the periodic noise because it is correlated with a time-delayed version of itself whereas the desired speech will remain because it is not similarly correlated with the delayed input.

In practice, it may be desirable to only use the filtered output of the summing block 100 when strong periodicity is detected. When weak or no periodicity is detected, the sub-band output is made equal to the sub-band input to avoid degradation of the signal. This periodicity detector may be made by allowing the sub-band filtering block to always operate while observing the variance of the filter coefficients. During regions where the variance is high, above a settable threshold, periodicity would be declared, activating a switch to the filtered output. Conversely, where the variance is low, below a settable threshold which may be different from the previous threshold to implement hysteresis, periodicity would be declared absent and switching the output to use the unfiltered input. Other versions are envisaged as well, where the periodicity detection is done with fuzzy logic and the output is a weighted sum of the filtered and unfiltered inputs according to the certainty of the periodicity detection.

The embodiments of the acoustic shock protection system act as an intelligent limiter, which quickly and accurately recognizes acoustic shock conditions and quickly eliminates the acoustic shock conditions. It can provide broadband and narrowband attenuation of the received signal. The system may limit the output levels from the headset to a specified maximum that is frequency dependent. The system may provide attenuation of sounds that is below the maximum outputs, but are significantly above the current average sound levels.

The pattern analysis-based approach of the present invention provides high fidelity and low group delay in the processed output signal relative to existing devices.

According to a further aspect of the embodiment of the present invention, an oversampled filterbank (e.g. WOLA filterbank) provides low-group delay and the ability to make large gain adjustments without adversely impacting signal fidelity or adjacent band signals. These combine to offer a high level of protection and high fidelity.

Further, calibration and personalization allow the system to be easily adjusted to work with a specific acoustic configuration (e.g. a specific headset or headphone). Built-in calibration software allows for simplified calibration in the field. Personalization allows some parameters of the invention to be adjusted by the user so that the performance and fidelity suit their specific preferences.

The embodiments of the present invention provide the ability to log data and download it for later analysis. This can be done over a wired or wireless (radio frequency or other) link. For example, the acoustic shock protection system can be connected to an IP network (and to the Internet) or it can use existing RF technologies, such as 802.11, Bluetooth or Zigbee. An addressing scheme allows the logging and analysis of data from multiple systems so that the invention can be used in an environment where a number of units need to have data logged and analyzed (e.g. a call center).

The embodiments of the acoustic shock protection system are applicable to telephone systems (both mobile and land), mobile and land-based radio systems, audio protection systems and similar devices, such as headsets or headphones, that protect users from loud sounds. Similar areas of technology include audio limiters and dynamic range compressors.

The embodiments described above may be implemented by any hardware, software or a combination of hardware and software having the above described functions. The software code, either in its entirety or a part thereof, may be stored in a computer readable memory. Further, a computer data signal representing the software code, which may be embedded in a carrier wave may be transmitted via a communication network. Such a computer readable memory and a computer data signal are also within the scope of the present invention, as well as the hardware, software and the combination thereof.

While particular embodiments of the present invention have been shown and described, changes and modifications may be made to such embodiments without departing from the true scope of the invention.

What is claimed is:

1. A method of providing protection against acoustic shock, the method comprising:
   receiving an input signal in a time domain at an acoustic shock protection device;
   performing a pattern analysis on the input signal, including:
      at an oversampled analysis filterbank, transforming the input signal to a plurality of band signals in a frequency domain, and
      performing a feature extraction from the input signal based on a fast average and a slow average of the input signal, and performing a feature extraction from the plurality of band signals based on a fast average and a slow average of each band signal, to identify a parameter space corresponding to a signal space of the input signal;
   applying a rule-based decision to the parameter space to detect an acoustic shock event, including:
      determining a shock flag based on each of the input signal and band signal feature extractions; and
   removing the acoustic shock event based on the shock flags.

2. A method as claimed in claim 1 wherein the step of removing the acoustic shock event includes the step of:
   performing gain control.

3. A method as claimed in claim 2 wherein the gain control is performed by a state machine.

4. A method as claimed in claim 1 further comprising the step of:
   at the acoustic shock protection device, performing calibration to keep an output signal provided to a user at a specific level.

5. A method as claimed in claim 1 further comprising:
   at the acoustic shock protection device, implementing on-line data collection of the acoustic shock event.

6. A method of providing protection against acoustic shock, the method comprising:
   receiving an input signal in a time domain at an acoustic shock protection device;
   performing a weighted overlap-add (WOLA) analysis on the input signal to transform the input signal to a plurality of band signals in a frequency domain;
   performing feature extraction from the input signal based on a fast average and a slow average of the input signal, and performing feature extraction from the band signals based on a fast average and a slow average of each band signal;
   detecting an acoustic shock event based on the input signal and band signal feature extractions, including:

determining a shock flag based on each of the input signal and band signal feature extractions, performing gain control based on the acoustic shock detection including the shock flags and the features extracted from the input signal and band signals, the band signals being modified by the gain control;

applying a calibrated gain to meet a predetermined safe output level; and performing a WOLA synthesis on the modified band signals to output an audio output signal from the acoustic shock protection device.

7. A method as claimed in claim 6 wherein the step of detecting an acoustic shock event uses a rule-based decision.

8. A method as claimed in claim 6 further comprising the step of:

delaying the input signal to the WOLA analysis to allow time to obtain fast broadband features to aid in the interpretation of the WOLA analysis results.

9. A system for providing protection against acoustic shock, the system comprising:

an analysis module for performing a pattern analysis on an input signal in a time domain, including:
an oversampled analysis filterbank for transforming the input signal to a plurality of band signals in a frequency domain, and
a feature extraction module for performing a feature extraction from the input signal based on a fast average and a slow average of the input signal, and performing a feature extraction from the plurality of the band signals based on a fast average and a slow average of each band signal, to identify a parameter space corresponding to a signal space of the input signal;

a detection module for applying a rule-based decision to the parameter space to detect an acoustic shock event, including:
a module for determining a shock flag based on each of the input signal and band signal feature extractions; and a removal module for removing the acoustic shock event based on the shock flags.

10. A system as claimed in claim 9 wherein the removal module performs gain control.

11. A system as claimed in claim 10 wherein the detection module includes a state machine for performing the gain control.

12. A system as claimed in claim 9 further comprising a removable module for logging the acoustic shock events.

13. A system as claimed in claim 9 further comprising a calibration module for performing calibration to keep an output signal provided to a user at a specific level.

14. A system as claimed in claim 9 further comprising a logging module for implementing on-line data collection of the acoustic shock event.

15. A system as claimed in claim 9 wherein the oversampled analysis filterbank comprises a weighted overlap-add analysis filterbank for transforming the input signal into a plurality of oversampled sub-band signals in a sub-band domain, and wherein the system comprises a weighted overlap-add synthesis filterbank for providing an output signal.

16. A system for providing protection against acoustic shock, the system comprising:

a weighted overlap add (WOLA) analysis module for transforming an input signal in a time domain to a plurality of band signals in a frequency domain;

a feature extraction module for performing feature extraction from the input signal based on a fast average and a slow average of the input signal, and for performing feature extraction from the band signals based on a fast average and a slow average of each band signal;

a detection module for detecting an acoustic shock event based on the input signal and band signal feature extractions, including:
a module for determining a shock flag based on each of the input signal and band signal feature extractions;

a gain control module for performing gain control based on the acoustic shock detection including the shock flags and the features extracted from the input signal and band signals, the band signals being modified by the gain control;

a calibration module for applying a calibrated gain to meet a predetermined safe level; and a WOLA synthesis module for synthesizing the modified band signals to provide an output signal.

17. A system as claimed in claim 16 wherein the detecting module detects the acoustic shock event using a rule-based decision.

18. A system as claimed in claim 16 further comprising a delay module for delaying the input signal to the WOLA analysis to allow time to obtain fast broadband features to aid in the interpretation of the WOLA analysis results.

19. A method as claimed in claim 8, further comprising the step of adjusting the delay time of the delaying step.

20. A method as claimed in claim 19, wherein the delay time is reduced to zero so that the inherent group delay of the WOLA analysis is used to provide the required delay.

21. A system as claimed in claim 18, further comprising means for adjusting the delay time of the delaying module.

22. A system as claimed in claim 21, wherein the delay time is reduced to zero so that the inherent group delay of the WOLA analysis is used to provide the required delay.

23. A method as claimed in claim 6, wherein the shock flags comprises:

a time domain shock flag based on the feature extraction from the input signal and, a narrowband shock flag based on the feature extraction from the band signal, wherein the step of performing gain control includes at least one of the following steps of:
calculating a broadband gain based on the feature extraction from the input signal and the time domain shock flag;
calculating a narrowband gain based on the feature extraction from the band signal and the narrowband shock flag;
calculating a gain weighting ratio based on the time domain shock flag, the narrowband shock flag and the extracted features of the input signal and band signals; and
calculating a gain for the gain control based on the broadband gain, narrowband gain, the weighting ratio and the narrowband shock flag.

24. A method as claimed in claim 23, further comprising the step of:

staring a broadband counter when the shock is detected in the time domain.

25. A method as claims in claim 24, wherein the broadband counter is used for calculating the broadband gain and the narrowband gain.

26. A method of providing protection against acoustic shock, the method comprising:

performing a weighted overlap-add (WOLA) analysis on an input signal in a time domain to transform the input signal to a plurality of band signal in a frequency domain;

delaying the input signal to the WOLA analysis to allow time to obtain fast broadband features to aid in the interpretation of the WOLA analysis results;

performing feature extraction from the input signal based on a fast average and a slow average of the input signal, and performing feature extraction from the band signals based on a fast average and a slow average of each band signal;

detecting an acoustic shock event based on the input signal and band signal feature extractions;

performing gain control based on the shock detection and the features extracted from the input signal and band signals, the band signals being modified by the gain control;

applying a calibrated gain to meet a predetermined safe output level; and performing a WOLA synthesis on the modified band signals to provide an output signal.

27. A method as claimed in claim 26, further comprising adjusting the delay time of the delaying step.

28. A method as claimed in claim 27, wherein the delay time is reduced to zero so that the inherent group delay of the WOLA analysis is used to provide the required delay.

29. A system for providing protection against acoustic shock, the device comprising:

a weighted overlap add (WOLA) analysis module for transforming an input signal in a time domain to a plurality of band signals in a frequency domain;

a delay module for delaying the input signal to the WOLA analysis to allow time to obtain fast broadband features to aid in the interpretation of the WOLA analysis results;

a feature extraction module for performing feature extraction from the input signal based on a fast average and a slow average of the input signal, and for performing feature extraction from the band signals based on a fast average and a slow average of each band signal;

a detection module for detecting an acoustic shock event based on the inputs signal and the band signal feature extractions;

a gain control module for performing gain control based on the shock detection and the features extracted from the input signal and band signals, the band signals being modified by the gain control;

a calibration module for applying a calibrated gain to meet a predetermined safe level; and a WOLA synthesis module for synthesizing the modified band signals to provide an output signal.

30. A system as claimed in claim 29, further comprising means for adjusting the delay time of the delaying module.

31. A system as claimed in claim 30, wherein the delay time is reduced to zero so that the inherent group delay of the WOLA analysis is used to provide the required delay.

* * * * *